(12) United States Patent
Seher et al.

(10) Patent No.: US 6,936,225 B2
(45) Date of Patent: Aug. 30, 2005

(54) PRESSURE-VARIATION FLUID TRANSPORT, IN PARTICULAR FOR BODY-FLUID ANALYSIS

(75) Inventors: Jens-Peter Seher, Stuttgart (DE); Gerhard Pross, Schoenbuch (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 330 days.

(21) Appl. No.: 09/911,125

(22) Filed: Jul. 23, 2001

(65) Prior Publication Data

US 2002/0094583 A1 Jul. 18, 2002

(30) Foreign Application Priority Data

Aug. 3, 2000 (EP) .............................................. 00116776

(51) Int. Cl.⁷ .............................. B01L 3/02; B01L 3/00; G01N 21/00; G01N 15/06
(52) U.S. Cl. ......................... 422/100; 422/102; 422/58; 422/68.1; 436/180
(58) Field of Search ................................ 422/100, 102, 422/58, 68.1; 436/180

(56) References Cited

U.S. PATENT DOCUMENTS

| | | | | |
|---|---|---|---|---|
| 4,748,564 A | * | 5/1988 | Matsuda ....................... 701/79 |
| 4,780,818 A | * | 10/1988 | Kubo ........................... 701/78 |
| 5,096,669 A | | 3/1992 | Lauks et al. ................... 422/61 |
| 5,279,294 A | | 1/1994 | Anderson et al. ............ 128/633 |
| 5,571,476 A | * | 11/1996 | Newman ....................... 422/26 |
| 5,599,301 A | * | 2/1997 | Jacobs et al. .................. 604/65 |
| 5,665,601 A | * | 9/1997 | Kilmer ......................... 436/54 |
| 5,725,831 A | * | 3/1998 | Reichler et al. ............... 422/56 |
| 5,783,148 A | * | 7/1998 | Cottingham et al. .......... 422/56 |
| 5,916,813 A | * | 6/1999 | Gorog ........................... 436/69 |
| 6,136,609 A | * | 10/2000 | Sato et al. .................... 436/180 |
| 6,162,395 A | * | 12/2000 | Kowanko ....................... 422/33 |
| 6,168,048 B1 | * | 1/2001 | Xu et al. ........................ 222/1 |
| 6,372,185 B1 | * | 4/2002 | Shumate et al. ............. 422/100 |
| 6,403,037 B1 | * | 6/2002 | Chang et al. ............... 422/68.1 |
| 6,489,171 B1 | * | 12/2002 | Aghassi et al. ............. 436/180 |
| 6,513,902 B1 | * | 2/2003 | Amano et al. ................. 347/23 |
| 6,623,088 B2 | * | 9/2003 | Roden et al. ............. 303/113.1 |
| 6,632,651 B1 | * | 10/2003 | Nevo et al. ............... 435/286.5 |
| 6,638,478 B1 | * | 10/2003 | Treu et al. ..................... 422/44 |
| 6,648,842 B2 | * | 11/2003 | Horkel ......................... 601/45 |
| 6,715,465 B2 | * | 4/2004 | Hallam ........................ 123/317 |
| 2002/0092489 A1 | * | 7/2002 | Mikame et al. ........... 123/90.17 |
| 2002/0127736 A1 | * | 9/2002 | Chou et al. ................. 436/180 |
| 2002/0182113 A1 | * | 12/2002 | Shvets et al. .................. 422/99 |
| 2002/0182115 A1 | * | 12/2002 | Aghassi et al. ............. 422/100 |
| 2003/0022391 A1 | * | 1/2003 | Richards et al. ............ 436/180 |
| 2004/0052689 A1 | * | 3/2004 | Yao ............................. 422/100 |
| 2004/0129478 A1 | * | 7/2004 | Breed et al. ................. 180/273 |
| 2004/0176671 A1 | * | 9/2004 | Fine et al. ................... 600/322 |
| 2004/0196339 A1 | * | 10/2004 | Kobayashi et al. ........... 347/85 |

FOREIGN PATENT DOCUMENTS

| | | |
|---|---|---|
| EP | 44 10 224 | 9/1995 |
| WO | WO 93/17328 | 9/1993 |

* cited by examiner

*Primary Examiner*—Jill Warden
*Assistant Examiner*—Brian R. Gordon
(74) *Attorney, Agent, or Firm*—Thomas M. Lundin

(57) ABSTRACT

A fluid movement system for moving a sample fluid is preferably included in a cartridge to be inserted into a reading device. The fluid movement system includes a pressure variation means for moving the sample fluid under the influence of a pressure variation applied to the fluid movement system, and a timing means for controlling the timing for releasing a pressure in the pressure variation means.

8 Claims, 8 Drawing Sheets

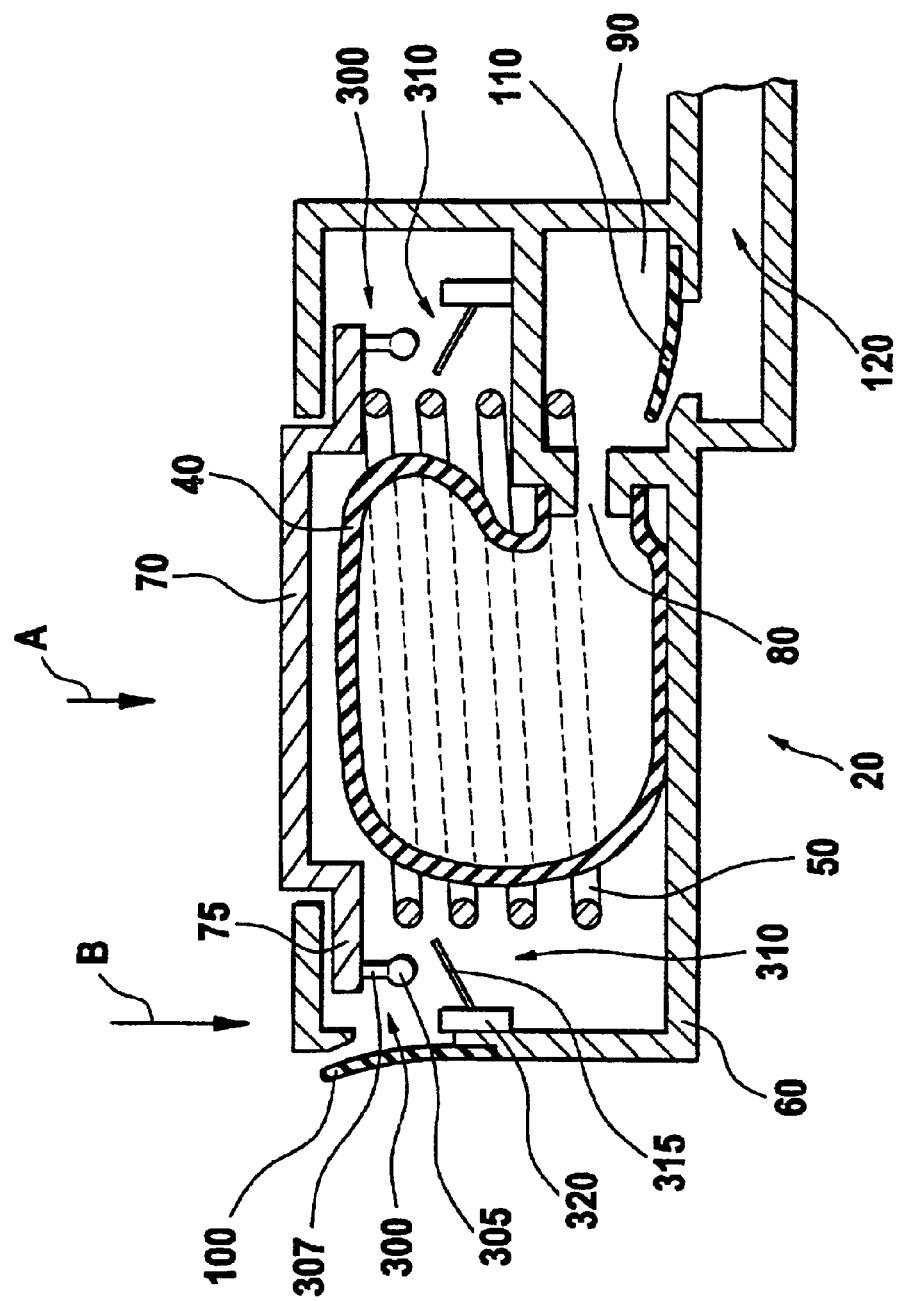

PRESSURE-VARIATION FLUID TRANSPORT, IN PARTICULAR FOR BODY-FLUID ANALYSIS

BACKGROUND OF THE INVENTION

1. Field of the Invention

The present invention relates to present transport of fluids, in particular for body-fluid analysis purposes.

2. Discussion of the Background

Testing of blood, or other body fluids, for medical evaluation in diagnosis has traditionally been domain of central laboratories offering efficient, reliable and accurate testing of a high volume of fluid samples. Samples must be collected, transported to the laboratory, analyzed and the result has then to be communicated back. This often produces delays of several days between sample collection and communication of the test results.

U.S. Pat. No. 5,096,669 discloses a system with a disposable device and a hand-held reader, which can perform a variety of electrochemical measurements on blood or other fluids. In operation, a fluid sample is drawn into the disposable device through an orifice by capillary action. The orifice is sealed off and the disposable device is inserted into the reader. The reader which controls the test sequence and flow of fluid causes a calibrant pouch located inside the device to be pierced, releasing the calibrant fluid to flow across the sensor arrays to perform calibration. Next, an air bladder located in the device is depressed, forcing the sample across the sensors where measurements are performed and read by the reader which performs the calibrations. Once the measurements are made, the device can be withdrawn from the reader and discarded. While in the first step the fluid sample has to be manually inserted into the disposable device, the reader further controls displacing the calibrant fluid as well as the fluid sample within the disposable device.

A further system, the IRMA SL Blood Analysis System, introduced by Agilent Technologies, also applies a disposable cartridge for analyzing body fluids in conjunction with a portable reading and evaluation unit. After inserting the cartridge into the reader, a calibration process of the sensor element within the cartridge by means of a calibration gel already situated on the sensor elements is initiated. When the calibration process has been finalized, the blood or other fluid sample has to be manually inserted into the cartridge during a defined time frame by means of a capillary-syringe collection device.

SUMMARY OF THE INVENTION

It is object of the present invention to further improve fluid transport in fluid analysis systems, in particular in cartridge-based fluid analysis systems e.g. for analyzing blood or other body fluids. The object is solved by the independent claims. Preferred embodiments are shown by the dependent claims.

According to the invention, pressure variation is used for moving one or more fluids. The pressure variation can be applied e.g. for moving a calibration fluid or gel, and/or for moving a fluid sample to be analyzed. In a cartridge-based fluid analysis system, the pressure variation is preferably introduced to the cartridge, preferably during insertion of the cartridge into a reading device, for moving one or more fluids within the cartridge.

The pressure variation can be an applied underpressure, overpressure, or a combination of underpressure and overpressure applied successively or in parallel to each other. Underpressure can be used for drawing the fluid, while overpressure might be applied for pushing the fluid, in particular when those fluids are moved in a capillary system.

The term 'capillary system' as used for the purpose of this invention shall mean any system applying capillary forces in order to keep fluids in position and/or to direct or move fluids in a predetermined way/direction, and shall cover any kind of shaping of the capillary channels, such as round, elliptical, square, etc. and combinations thereof.

The term 'drawing' the fluid shall represent a situation where the fluid-moving force is substantially resulting from a 'location ahead of the fluid' in the direction of movement. This can be achieved e.g. by applying a suction force and/or using the principle of a water jet pump. The term 'pushing' the fluid, accordingly, shall represent a situation where the fluid-moving force is substantially resulting from a 'location behind the fluid' with respect to the direction of movement. This can be achieved e.g. by applying an overpressure to an air bladder (or air bubbles) 'behind' the fluid in a capillary, thus moving the fluid in the direction in the direction of the applying force on the air bladder.

A combination of overpressure and underpressure allows achieving a two- or more-step process, wherein e.g. in a first step fluid is moved under influence of the overpressure by pushing the fluid. Preferably by applying valve systems, releasing the overpressure by pushing the fluid can be used for setting up an underpressure. Releasing the underpressure might then be used for transporting this or a different fluid, e.g. by drawing the fluid under influence of the underpressure. In such a two-step approach, the first step for transporting under influence of overpressure can be applied for moving a calibration fluid/gel to or away from the sensors. The second step of transporting fluid under the influence of underpressure can then successively be applied for moving the sample fluid to be analyzed to or away from the sensors. However, it is clear, that both steps can also be applied individually and independently of each other.

The pressure variation can be caused preferably by a manual activation, such as manually pressing, pushing or pulling by hand, or by an automatic activation controlled e.g. by the reading device. The pressure variation process is preferably initiated when a cartridge is coupled to or inserted into the reading device. In case of manual activation, the user might then be prompted to execute the manual activation (e.g. pushing on a press button). In case of automatic activation, the reading device might start the activation after the cartridge has been coupled to or inserted. This might be in conjunction with a process for locking the cartridge against prematurely removing from the reading device. In this case, means for locking the cartridge might be applied for pushing e.g. a suitable press button, thus locking the cartridge and concurrently activating the pressure variation.

In a preferred embodiment, the pressure variation is accomplished by a volumetric decrease and/or increase. For that purpose, the cartridge preferably comprises a pressure chamber which can be compressed, thus decreasing or increasing the volume of the pressure chamber. The volumetric decrease/increase leads to an overpressure/ underpressure within the pressure chamber. The overpressure/underpressure in the pressure chamber can then be applied for fluid moving or simply be released, dependent on the specific application.

The pressure chamber may have several separated chambers, so that a pressure variation can be applied to one or more of the chambers concurrently of successively.

Preferably, all chambers can be decreased/increased in volume in one step, but might be released with different timings, e.g. successively. Such an embodiment allows to accomplish different timing steps e.g. for calibration and/or measurement.

It is technically clear that the term 'chamber' as used herein is to be understood in its broadest sense and does not require a specific or separated room solely for the purpose of pressure activation. The term 'chamber' shall simply denote any kind of physical 'room' that allows to at least temporarily changing the pressure conditions against its environment. Chamber thus can mean e.g. an entire conduit system but also a more or less separated room only.

The pressure chamber preferably comprises a resilient member, such as a membrane and/or a rubber bellow preferably e.g. supported by a spring mechanism, which will then counteract a force applied onto the resilient member in order to decrease/increase volume of the pressure chamber. Once the resilient member has been pressed down for volumetric compression or pulled out for volumetric expansion, the resilient member will then try to return into its initial position. This can then be used for providing an underpressure/overpressure in the pressure chamber after the overpressure/underpressure in the pressure chamber has been released. In other words, as soon as the overpressure/underpressure will be released, as long as the resilient member is pressed down/pulled up, the reverse movement of the resilient member will lead to a volumetric increase/decrease, thus building up an underpressure/overpressure within the pressure chamber. The change between overpressure and underpressure within the pressure chamber is preferably supported by means of adequate valve means. Releasing the underpressure/overpressure in the pressure chamber may then be applied for fluid movement, e.g. by drawing and/or pushing the fluid in a corresponding conduit system.

In a further preferred embodiment, the overpressure achieved by pressing down the resilient member of the pressure chamber will be immediately used for a first fluid movement, preferably for moving the calibration fluid to or away from the sensor elements. This can be achieved in that the overpressure in the pressure chamber will be (preferably immediately) released, thus pushing the fluid(s) in a capillary system such as a conduit system. Once the overpressure is released, the resilient member wants to return in its initial position. As long as the gas flow into the pressure chamber will be limited or completely avoided, e.g. by means of a valve or a mechanical spring load, this will lead to a constant or slowly decreasing underpressure in the pressure cell. Opening the valve or releasing the spring load will then release the underpressure in the pressure chamber, which can be applied for further fluid movements, preferably for moving the sample fluid to the sensor elements. The above applies accordingly when first an underpressure is generated e.g. by pulling out the resilient member.

Controlling the point in time for releasing the pressure (underpressure or overpressure) in the pressure chamber can be applied for controlling a timing sequence e.g. of calibration and measuring processes. This in particular is useful since most systems require a certain calibration time (e.g. some seconds up to two minutes) until the analysis system is ready for measuring the fluid sample. The timing sequence is preferably defined by controlling a valve system e.g. by means of mechanical or electrical timing means. Electrical timing means can be, for example, an electrical current subjected to the valve, which will eventually destroy or otherwise open the valve, thus releasing the pressure in the desired way. Mechanical timing means can be, for example, springs or pistons.

Releasing the pressure can be provided substantially instantaneous, i.e. in a time relatively short with respect to a time for providing or maintaining the pressure, or substantially continuously, i.e. in a time relatively long with respect to a time for providing or maintaining the pressure. In the former case, a valve might simply open up against environment, whereby the dimension of the opening against the environment is preferably selected in a way that substantially no flow restriction occurs. In the latter case, the dimension of the opening against the environment of the valve might be selected that flow restriction is dominating, so that a pressure balance between the pressure chamber and the environment will take some time.

Releasing the pressure in the pressure chamber can be preferably controlled in a way that movement of the sample fluid to the sensor elements will first be allowed after the calibration process has been finalized. In one embodiment, the pressure control is provided by the reading device, e.g. in that the reading device sends a signal or initiates e.g. a mechanical action after it has sensed the calibration process is done. In a further embodiment, the pressure control is provided by the cartridge independently of the reading device. This can be achieved e.g. by an electrical and/or mechanical timer system such as a clock or winded up mechanical clock.

Instead of controlling the sample fluid movements under consideration of the actual state of the calibration process, a fixed timing can be defined, so that the pressure will be released after a fixed period of time, independent of the actual state of the calibration process. By defining this fixed time period to cover at least the maximum expected calibration time, it can be made sure that the calibration process can be completely and independently executed and that no interference of the measurement process with the calibration process occurs.

It is clear that the invention can be partly or entirely embodied by one or more suitable software programs, which can be stored on or otherwise provided by any kind of data carrier, and which might be executed in or by any suitable data processing unit. Such software programs might be used, in particular, for controlling timing of the fluid movement, application of the pressure variation, and/or analyzing the fluids.

BRIEF DESCRIPTION OF THE DRAWINGS

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

FIGS. 3A–E illustrate details of an example for the pressure generation scheme.

DETAILED DESCRIPTION OF THE INVENTION

Figure 1:
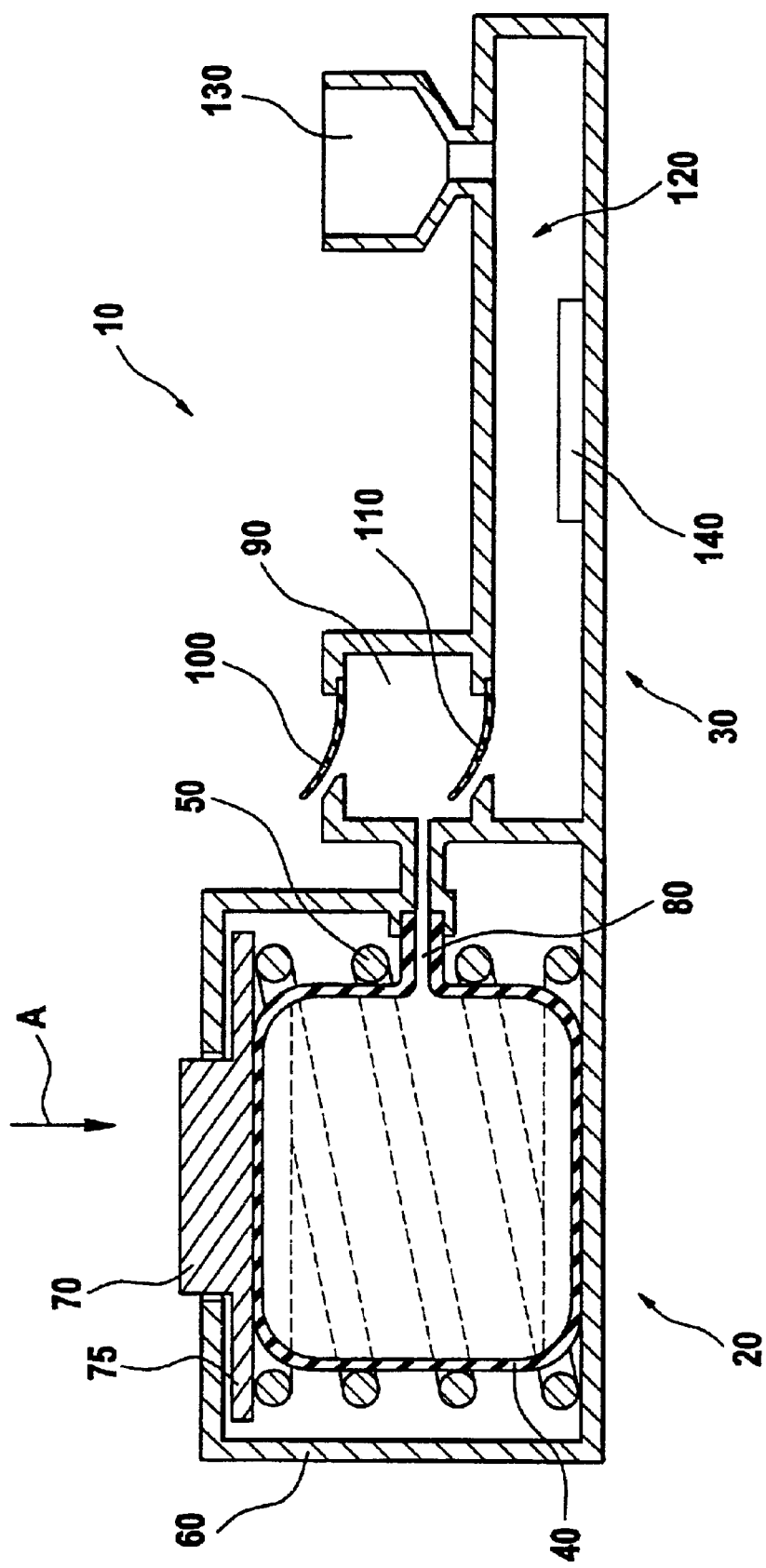
FIGS. 1 and 2 show examples of an embodiment of a fluid movement system 10 according to the invention.

FIG. 1 shows a first example of an embodiment of a fluid movement system 10 according to the invention. The fluid movement system 10 is preferably used for analyzing body fluids, in particular blood. However, it is clear, that the principles of the invention can be applied accordingly to any other system wherein fluids have to be moved, e.g. in a capillary system.

The fluid movement system 10 comprises a pressure generation unit 20 and a fluid movement area 30. The pressure generation unit 20 comprises a rubber bellow 40 supported by a spring 50. In this example, the spring 50 surrounds the rubber bellow 40, so that pushing or pulling the rubber bellow 40 has to be done against the restoring force of the spring 50. The rubber bellow 40 and the spring 50 are situated in a housing 60, whereby a movable press button 70 is situated in an opening on the upper side of the housing 60. The press button 70 attaches the rubber bellow 40 on its upper side, and might also be connected therewith.

The rubber bellow 40 is connected, preferably via a channel 80 that might also be part of the rubber bellow 40, to a valve chamber 90 as a further part of the pressure generation unit 20. The valve chamber 90 has a first valve 100 opened towards environment (i.e. outside of the fluid movement system 10), and a second valve 110 opened towards the fluid movement area 30. Both valves 100 and 110 are preferably flap valves. However, it is clear that any other valve type supporting the functioning of the fluid movement system 10, as described below, can be applied accordingly and might be selected dependent on criteria such as prize, ease of use, reliability or precision.

The rubber bellow 40 in conjunction with the mechanism of the spring 50 and the valves 100 and 110 constitutes a pressure chamber, which generally allows generating and maintaining a pressure, such as overpressure or underpressure, against the environment of the fluid movement system 10. Details will be shown and explained later.

The fluid movement area 30 comprises a sensor area 120 coupled (in the example of FIG. 1: abutting) to the valve chamber 90 via the second valve 110. The sensor area 120 is further coupled to a sample area 130 for receiving a fluid sample to be analyzed within the sensor area 120. Sensor elements 140 are located in the sensor area 120.

For operating the fluid movement system 10, a fluid sample is placed into (e.g. filled in) the sample area 130 and will be kept there, preferably under the influence of capillary forces or by additional valves. Because there is no initial pressure difference inside of the fluid movement system 10 with respect to its environment, capillary force might be enough to prevent the sample fluid in the sample area 130 from dropping into the fluid movement area 30 before an underpressure is applied.

In the initial position of the fluid movement system 10, as shown in FIG. 1, the rubber bellow 40 will be opened under the influence of the spring 50. The spring 50 also presses an inner flange 75 of the press button 70 against the inner top wall of the housing 60, thus acting as a stopper for the press button 70. The rubber bellow 40 thus has its maximum volume in this initial position.

For moving the sample fluid, located into the sample area 130, to the sensor area 120, the press button 70 will be pressed into the direction of arrow A, thus forcing the rubber below 40 to decrease its volume. The volume decrease of the rubber bellow 40 leads to an overpressure therein and thus into the valve chamber 90, which, again, closes the second valve 110 and opens the first valve 100, so that the overpressure can be released to the environment.

When the force into the direction of the arrow A will be removed, the spring 50, which has also been pressed down, will force the rubber bellow 40 to return into its initial position. This volume increase of the rubber bellow 40 driven by the spring 50 will lead to an underpressure in the rubber bellow 40 and thus into the valve chamber 90, which closes the first valve 100 and opens the second valve 110. This leads to an underpressure in the sensor area 120, which again will draw fluid of the fluid sample located in the sample area 130 into the sensor area 120 to the sensor elements 140.

The volume of the rubber bellow 40 should preferably be adjusted to the volume of the sample area 130, so that by releasing the underpressure, calibration fluid located over the sensor elements 140 can be completely removed and substituted by sample fluid. In case that e.g. a calibration fluid or gel has been situated on the sensor elements 140, it will also be removed from the sensor elements 140 under the influence of the underpressure.

Figure 2:
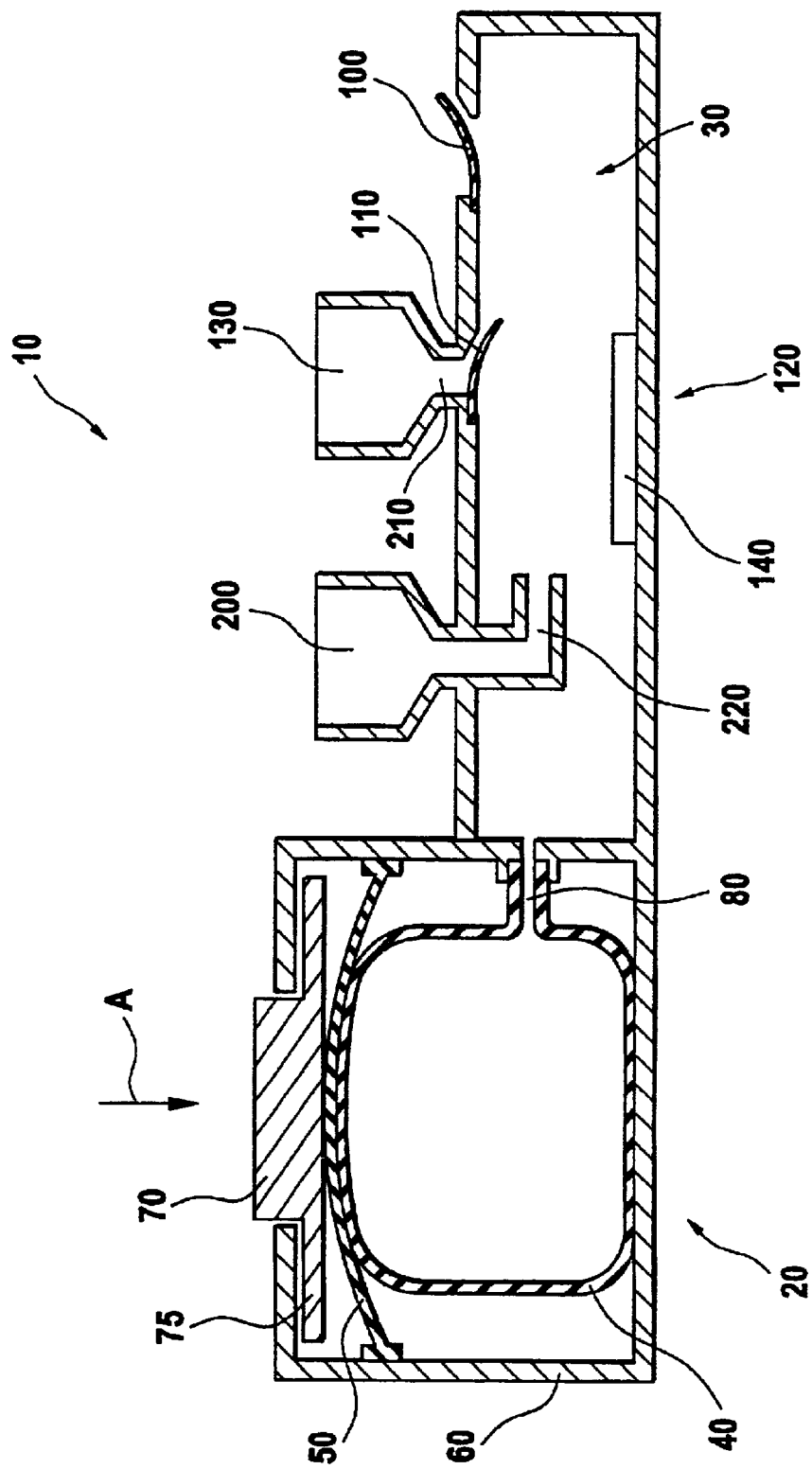

FIG. 2 shows another embodiment of the fluid movement system 10 according to the invention. While the embodiment of FIG. 1 only provides one sample area 130 with sample fluid to be moved into the sensor area 120, the fluid movement system 10 of FIG. 2 further provides a second sample area 200. As in FIG. 1, the first sample area 130 uses an underpressure generated by the rubber bellow 40 to move fluid (contained in the first sample area 130) into the sensor area 120. In contrast to FIG. 1, however, the embodiment of FIG. 2 further utilizes the overpressure, as generated by pushing down the press button onto the rubber bellow 40, to move fluid contained to the second sample area 200 to the sensor area 120.

Other differences are that the spring 50 in the embodiment in FIG. 2 is a membrane type spring. Further, the channel 80 in FIG. 2 opens directly to the sensor area 120 thus omitting the valve chamber 90. The first valve 100 and the second valve 110 are now located at the end of the sensor area 120. As in FIG. 1, the first valve 100 opens or closes towards the environment outside of the fluid movement system 10. The second valve 110 opens or closes a connection 210 of the first sample area 130 towards the sensor area 120. The first valve 100 is situated in a way that an overpressure in the sensor area 120 will close the second valve 110 and open the first valve 100. In the example of FIG. 2, the first valve 100 is situated in the air stream from the bellow 40 'behind' the connection 210.

In operation, pushing the press button 70 into the direction of the arrow A will cause an overpressure into the rubber bellow 40 and accordingly into the sensor area 120, so that the first valve 100 will open and the second valve 110 will close. Since an opening 220 of the second sample area 200 towards the sensor elements 140 is located in-between an airflow directed from the rubber bellow 40 over the channel 80 and the sensor area 120 to the (opened) first valve 100, sample fluid located into the second sample area 200 will be drawn into the sensor area 120 to the sensor elements 140, e.g. in the sense of a water jet pump. In principle, the overpressure flow around the (capillary) opening 220 of sample area 200 will suck sample fluid out of sample area 200 and into the sensor area 120 to the sensor elements 140.

When the force into the direction of the arrow A will be released, the (membrane) spring 50 will force the rubber bellow 40 to return into its initial position, thus generating an underpressure into the rubber bellow 40 and accordingly into the sensor area 120. Under the influence of the underpressure into the sensor area 120, the first valve 100 will close and the second valve 110 will open, thus clearing the connection of the first sample area 130 via the connection 210 into the sensor area 120. Fluid contained into the first sample area 130 will then be drawn under the influence of the underpressure into the sensor area 120 to the sensor elements 140. Since the sensor elements 140 are located between the connection 210 and the opening 220, no further fluid from the second sample area 200 or the opening 220 will be directed towards the sensor elements 140. The embodiment of FIG. 2 thus uses the underpressure as well as the overpressure as generated into the rubber bellow 40 for moving different fluid samples in the sensor area 120.

It is clear that by providing adequate conduits and/or suitably forming the parts of the fluid movement area 30, the fluid movement into the fluid movement system 10 can be directed and controlled as required. For the sake of simplicity and also since FIGS. 1 and 2 only represent the drawings for illustrating the principles of the invention, details for guiding and controlling the fluid flow have been omitted.

FIG. 3A shows another embodiment of the invention. The pressure generation units 20 of FIG. 3A and FIGS. 1–2 substantially correspond to each other with the difference that in FIG. 3A the chamber 90 between the rubber bellow 40 and the sensor area 120 is integrated into the housing 60. While the first valve 100 could also have been provided e.g. at the right side wall of the housing 60, it is situated in FIG. 3 on the left side wall of the housing 60. This also illustrates that there are many variations possible to arrange the valve(s) without departing from the idea of the invention.

While insofar the embodiment of FIG. 3A does not go beyond the principles as illustrated with respect to FIGS. 1 and 2, the pressure generation units 20 of FIG. 3 further provides means for controlling the timing for moving the fluid(s). For that purpose, the press button 70 further comprises hooks 300 at its lower end. Corresponding locking means 310 are provided at the housing 60.

In the example of FIG. 3, each hook 300 comprises a ball 305 situated on a rod 307 having a smaller diameter than the outer diameter of the ball 305. Each locking means 310 comprises a spring-loaded leaf 315 with an opening 317 having a first shaping 318 allowing to receive the ball 305 and a second shaping 319 that cannot receive the ball 305. The leaf 315 is coupled to a spring clock mechanism 320.

Figure 3B:
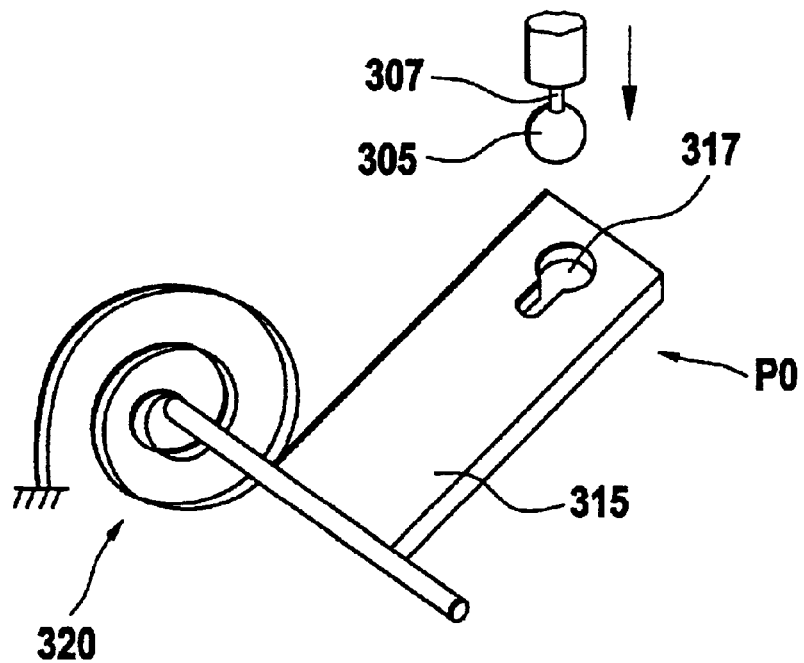
Figure 3C:
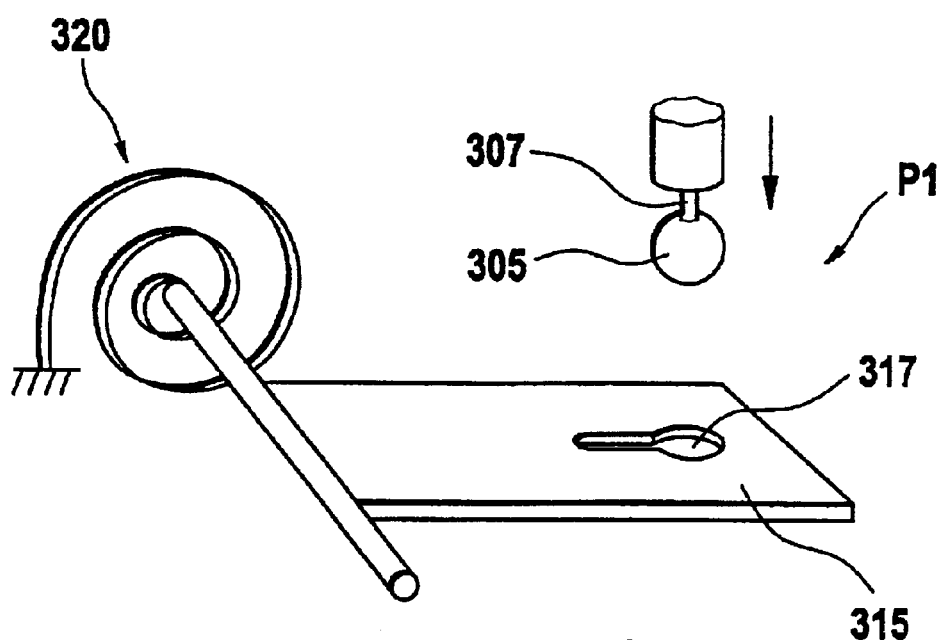
Figure 3D:
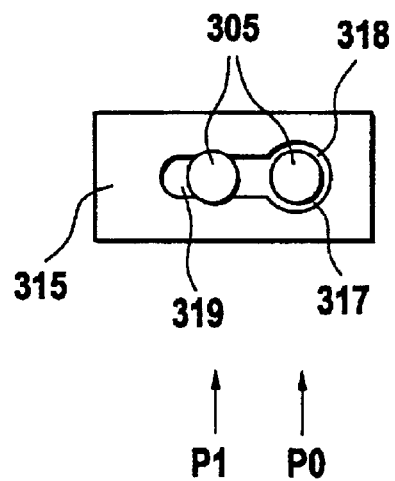
Figure 3E:
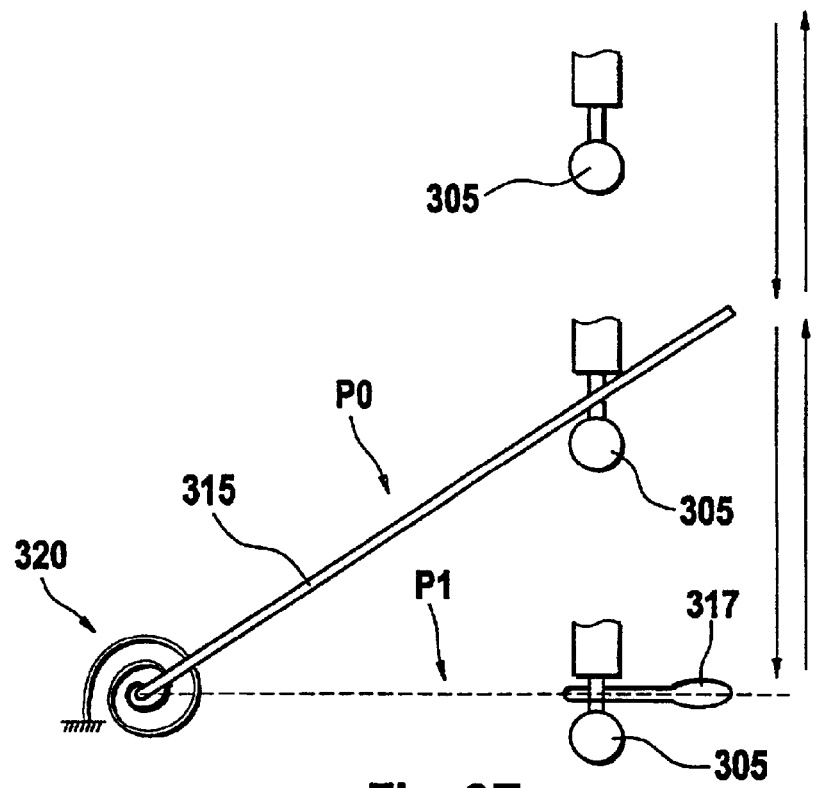

FIGS. 3B, 3D and 3E depict an initial position P0 of the locking means 310, wherein the leaf 315 is angled towards the hook 300. In that initial position P0, the ball 305 will 'see' the first shaping 318 of the opening 317, and can penetrate through when lowered in direction of angle A. However, once entered through the opening 317, the hook 300 (e.g. in combination with the flange 75 or other parts of the press button 70) will move the leaf 315 further towards a position P1. In this position P1 (cf. FIGS. 3C–E), the rod 307 is located within the second shaping 319.

Once the pressure on the press button 70 in direction of arrow A will be removed, the spring 50 will force the press button 70 in its initial position. However, the spring clock mechanism 320, which has been activated when forcing from position P0 into position P1, will first keep the leaf 315 in the position P1 and slowly release to return to position P0. In a preferred embodiment, the spring clock mechanism 320 comprises a spring together with a gear mechanism, which when wound up will slowly return into its initial position, whereby the returning speed is dependent on the gear setting. Such mechanisms are well known in the art and need not be discussed here in detail.

As soon as the leaf 315 returns to position P0, the first shaping 318 of the opening 317 will release the ball 305 from the leaf 315, so that the press button 70 can also return into its initial position.

In other words, the shaping of the locking means 310 is provided in a way that when the hook 300 lowers towards the locking means 310, the hook 300 will first touch the locking means 310 in a first position that will not engage the hook 300. When the hook 300 is further moved into the direction of the arrow B, the locking means 310 will be forced under the influence of the hook 300 into a second position engaging the hook 300, so that it cannot return into its initial position once the force in direction of arrow A will be removed. The hook 300 will be locked e.g. by the converging opening 319 into the second position. Thus, the press button 70 will be kept down into a press down position and can first return to its initial position when the locking means 310 will release the hook(s) 300. Controlling the release of the hooks 300 will therefore allow controlling the timing of the underpressure phase when the rubber bellow 40 will return into its initial position (thus generating an underpressure). By means of an external force, e.g. bending or moving the locking means 310, the hooks 300 can be released to initiate the underpressure. This external force can be controlled by the fluid movement system 10 itself or by a reading device.

Instead as shown in FIG. 3A, the valves 100 and 110 can also be provided as depicted in FIG. 2, thus enabling to utilize the overpressure as well as the underpressure phase.

FIG. 4 illustrate another example for the interaction between the hook 300 and the locking means 310. In this example, a conical shaping 330 (referred to as cone 330) replaces the ball 305, also situated on the rod 307 having a smaller diameter than the outer diameter of the cone 330. Each locking means 310 comprises the spring-loaded leaf 315 with the opening 317 allowing to receive the cone 330. The leaf 315 is coupled to a spring 340. The locking means 310 further comprises a releasing means 350 having a locker 355 coupled to a timing means 360.

Figure 4A:
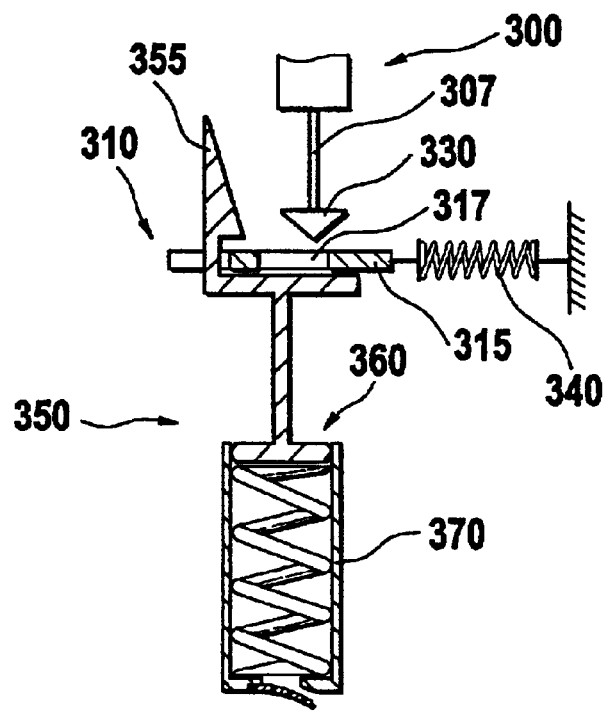
FIGS. 4A–E illustrate details of an example for providing a timing scheme for releasing pressure.
Figure 4B:
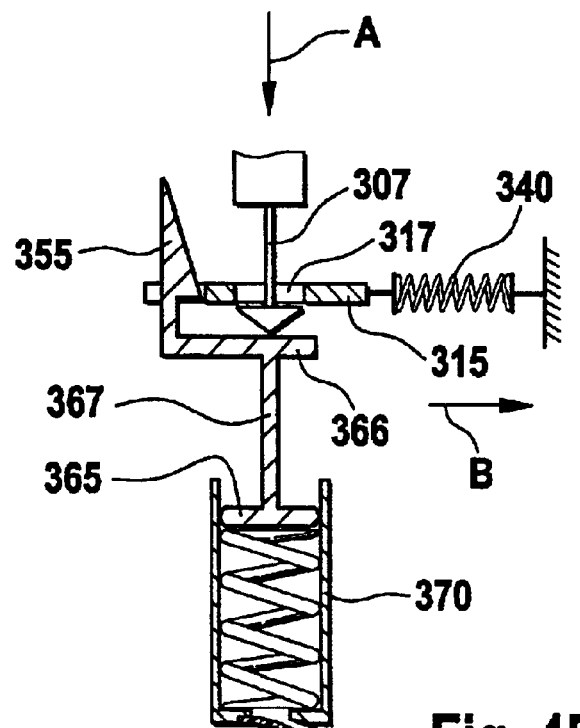
Figure 4C:
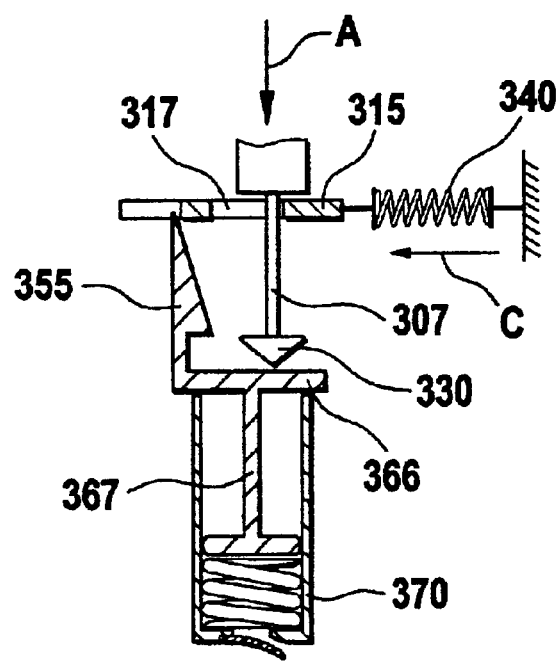

In FIG. 4A, the hook 300 and the locking means 310 are in their initial position. In FIG. 4B, the hook 300 has been lowered (direction of arrow A) towards the locking means 310, whereby the cone 330 has moved the leaf 315 into the direction of arrow until the cone 330 can enter through the opening 317. Once the cone 330 enters through the opening 317, the spring 340 will push the leaf 315 back into direction of arrow C, as shown in FIG. 4C. In this position, the cone 330 is locked by the leaf 315 and could not be withdrawn from the locking means 310 into the direction against arrow A.

Starting from the position as shown in FIG. 4B, the cone 330 pushes down a plunger 365 via a face 366 and a rod 367, when the cone 330 is further moved into the direction of arrow A. The plunger 365 can thus moved into a cylinder 370 against the force of a spring 375 in the cylinder 370, until an end position is reached as shown in FIG. 4C.

Figure 4D:
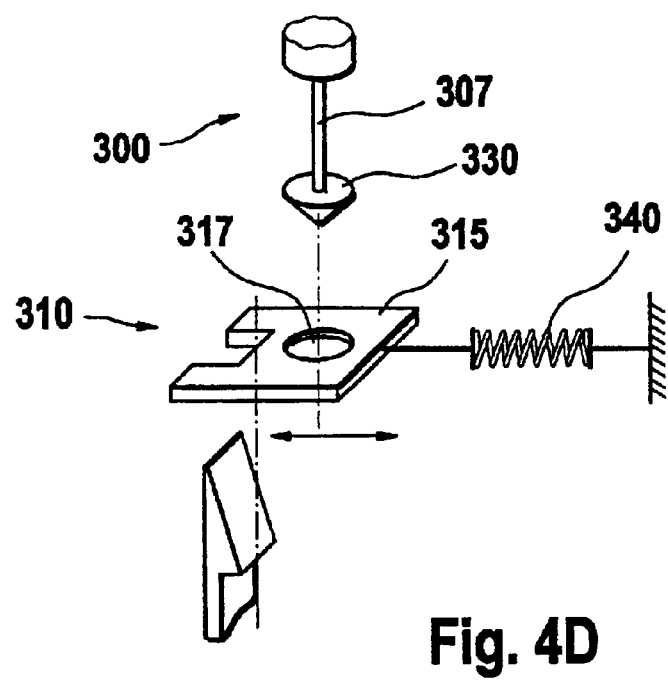
Figure 4E:
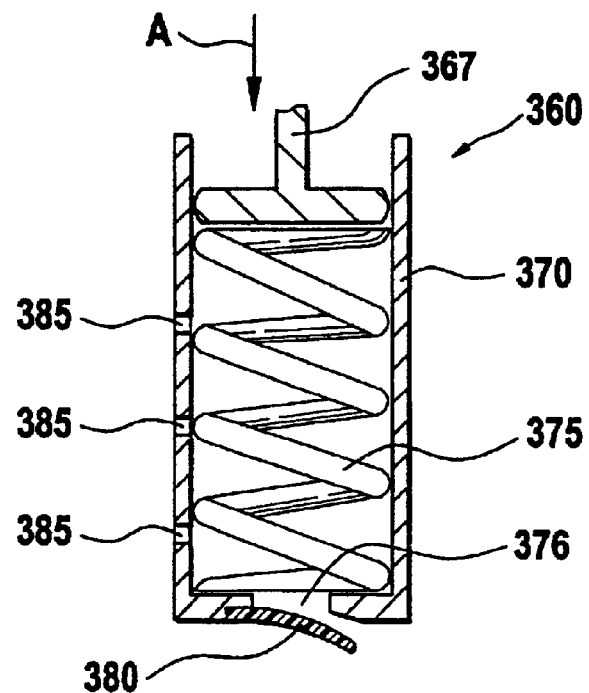

FIG. 4E shows the timing means 360 in greater detail. The cylinder 370 has an aperture 376 that can be opened or closed by a valve 380. When the plunger 367 is moved into the direction of arrow A, the thus created overpressure will open the valve 380 and release air out of the cylinder 370. When the force into the direction of arrow A is removed, the spring 375 will push the plunger 367 back against the direction of arrow A. The created underpressure in the cylinder 370 will close the valve 380, so that this underpressure cannot be immediately released and will counteract the force of the spring 375. In order to slowly release the underpressure, the cylinder 370 has at least one further opening 385 allowing an airflow into the cylinder 370. By designing the seize of the opening 385, determined e.g. by the cross section and the number of the openings 385, the time for releasing the plunger 367 and thus the entire locking means 310 back into the position as shown in FIG. 4B can be determined.

The locking means 310 when moved back into the position as shown in FIG. 4B will also push back the hook 300 as shown in FIG. 4B. In this position, the locker 355 will also open the locking of the cone 330 by the leaf 315, so that the hook 300 can then be moved back into the position of FIG. 4A.

FIG. 4D further shows parts of the locking means 310 together with the hook 300 in three dimensional view.

Figure 5:
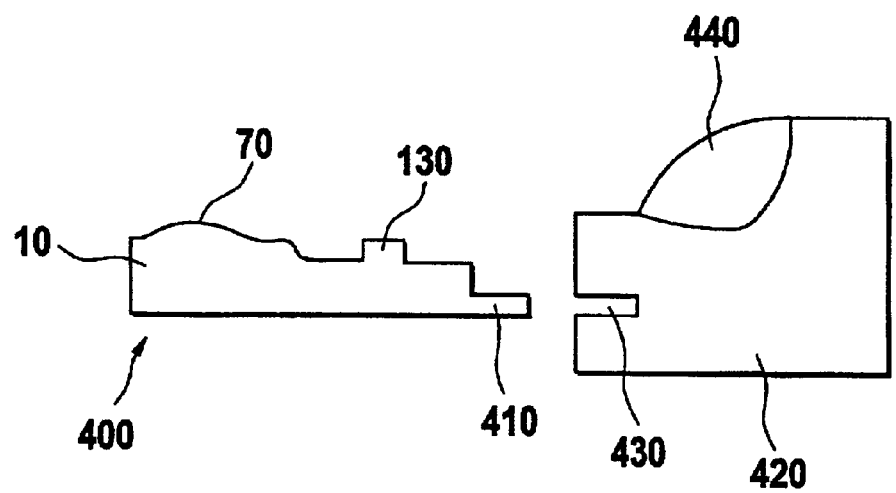
FIG. 5 shows an application of the invention for fluid movement into a cartridge 400 to be inserted into a reading device 420.

As depicted in FIG. 5, the fluid movement system 10 might be part or integrated into a (disposable) cartridge 400 with contacts 410 to couple to a reading device 420. The contacts 410 are coupled to the sensor elements 140, thus allowing to connect the electrical signals of the sensor elements 140 to a reading device 420. The reading device 420 converts electrical signals of the sensor elements 140 into concentration values, which can be output on a display 440.

Pressing down the press button 70 of the fluid movement system 10 in FIGS. 1–3 can be done manually, but also automatically, e.g. forced by the reading device 420. Preferably, the press button 70 will be pressed down when the fluid movement system 10 will be connected to the reading device 420, e.g. by inserting the fluid movement system 10, or parts thereof into a slot 430 of the reading device 420. In case of manual pressure, the reading device 420 might display on the display 440 a request to the user to press down the press button 70 for initiating the (calibration and) analyzing process. In case of automatic pressure application, the reading device 420 might push onto the press button 70 once the fluid movement 10 has been inserted or otherwise coupled to the reading device 20. It is clear that this kind of automatic process can also be applied for locking the fluid movement system 10 from being prematurely removed from the reading device 420 before the measurement has been completed.

What is claimed is:

1. A fluid movement system for moving a sample fluid comprising: a fluid container, pressure variation means for moving the sample fluid from the fluid container into a chamber under the influence of a pressure applied to the fluid movement system, and timing means for controlling the timing for releasing a pressure in the pressure variation means wherein the pressure variation means comprises a volume-variation means for generating an overpressure and/or an underpressure by adjusting the volume thereof, and wherein the pressure variation means further comprises a resilient member for counter-acting against the volumetric variation applied to the volume-variation means.

2. The fluid movement system of claim 1, further comprising a sensing element for sensing the sample fluid, wherein the pressure variation means is arranged for moving the sample fluid from and/or to the sensing element.

3. The fluid movement system of claim 1, further comprising fluid guiding means for guiding the sample fluid.

4. The fluid movement system of claim 1, wherein the pressure variation means further comprises at least one valve.

5. The fluid movement system of claim 1, wherein the volume-variation means is adapted to for successively generate an overpressure and/or an underpressure by adjusting the volume thereof, and a first valve for releasing the overpressure and/or for at least temporarily maintaining the underpressure.

6. The fluid movement system of claim 5, further comprising:
a second valve for securing the sample fluid against movement as long as the overpressure is maintained and/or for allowing the sample fluid to move as long as the underpressure is maintained.

7. A system comprising: a cartridge, a reading device, and the fluid movement system of claim 1, wherein said fluid movement system is included in said cartridge which is to be inserted into said reading device.

8. The fluid movement system of claim 1, further comprising fluid guiding means for guiding the sample fluid by means of capillary forces.

* * * * *